United States Patent [19]

Ford et al.

[11] Patent Number: 5,723,135
[45] Date of Patent: Mar. 3, 1998

[54] ONE-PHASE PROCESS FOR MAKING A CLEAR ANTIPERSPIRANT STICK CONTAINING DIBENZYLIDENE ALDITOL

[75] Inventors: Andrew Ford, Stoneham; David S. Wells, Shrewsbury, both of Mass.

[73] Assignee: The Gillette Company, Boston, Mass.

[21] Appl. No.: 588,619

[22] Filed: Feb. 6, 1996

[51] Int. Cl.$^6$ ................................................ A61K 7/00
[52] U.S. Cl. ........................ 424/401; 424/65; 424/66; 424/68; 424/47
[58] Field of Search .................... 424/401, 65, 66, 424/68, 47; 514/944

[56] References Cited

U.S. PATENT DOCUMENTS

| | | | |
|---|---|---|---|
| H1473 | 8/1995 | Orofino et al. | 424/67 |
| 3,981,986 | 9/1976 | Rubino | 424/47 |
| 4,017,599 | 4/1977 | Rubino | 424/47 |
| 4,154,816 | 5/1979 | Roehl et al. | 424/68 |
| 4,346,079 | 8/1982 | Roehl | 424/65 |
| 4,383,988 | 5/1983 | Teng et al. | 424/68 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabateili | 424/65 |
| 4,948,578 | 8/1990 | Burger et al. | 424/68 |
| 4,954,333 | 9/1990 | Ward | 424/66 |
| 5,106,999 | 4/1992 | Gardlik et al. | 549/364 |
| 5,162,378 | 11/1992 | Guthauser | 514/785 |
| 5,200,174 | 4/1993 | Gardlik et al. | 424/66 |
| 5,270,034 | 12/1993 | Cheng | 424/68 |
| 5,286,755 | 2/1994 | Kauffmann et al. | 514/944 |
| 5,346,694 | 9/1994 | Juneja | 424/66 |
| 5,368,848 | 11/1994 | Brazinsky et al. | 424/65 |
| 5,376,363 | 12/1994 | Benfatto et al. | 424/66 |
| 5,405,605 | 4/1995 | Shin | 424/68 |
| 5,463,098 | 10/1995 | Giovanniello et al. | 556/27 |
| 5,490,979 | 2/1996 | Kasat et al. | 424/66 |

FOREIGN PATENT DOCUMENTS

| | | | |
|---|---|---|---|
| 0 260 030 B1 | 6/1988 | European Pat. Off. | A61K 7/32 |
| 0 404 532 A1 | 12/1990 | European Pat. Off. | A61K 7/32 |
| WO 91/15191 | 10/1991 | WIPO | A61K 7/38 |

OTHER PUBLICATIONS

Klepak, "Antiperspirants take a clear lead", *Manufacturing Chemist* (Nov. 1994), pp. 31–36.
Disorbene, Roquette product brochure (1992).

Primary Examiner—Thurman K. Page
Assistant Examiner—D. Faulkner
Attorney, Agent, or Firm—Stephan P. Williams

[57] ABSTRACT

The present invention features a method of making a gel cosmetic stick. The method comprises first mixing a particulate dibenzylidene alditol with a liquid vehicle which contains an antiperspirant salt dissolved therein to form a uniform dispersion. The dibenzylidene alditol is mixed with the liquid vehicle at a temperature sufficiently low, preferably below 50° C., so that substantially none of the dibenzylidene alditol dissolves in the liquid vehicle. This dispersion may comprise a commercial size quantity, typically greater than 200 kg. A portion of this dispersion, typically a relatively small portion, is then heated to a temperature sufficient to dissolve the dibenzylidene alditol therein, then cooled to form a gel. This heating and cooling is conducted sufficiently rapidly so as to minimize degradation of the dibenzylidene alditol. Preferably the heating and cooling is conducted such that said portion is subjected to a temperature greater than 90° C. for not more than two hours, most preferably not more than thirty minutes.

23 Claims, No Drawings

ONE-PHASE PROCESS FOR MAKING A CLEAR ANTIPERSPIRANT STICK CONTAINING DIBENZYLIDENE ALDITOL

BACKGROUND OF THE INVENTION

The invention relates to a process for making clear gel cosmetic sticks which include a solubilized antiperspirant salt.

Gel antiperspirant sticks typically include a liquid vehicle, an antiperspirant salt, a gelling agent, and one or more emollients. Dibenzylidene alditols like dibenzylidene sorbitol (DBS), also known as dibenzylidene monosorbitol acetal (DBMSA), are one type of gelling agent that has been used in such sticks. Dibenzylidene alditols may degrade during manufacture and subsequent storage of the gel stick, in part because of the presence of the acidic antiperspirant salt in the stick. One product of the degradation, benzaldehyde, can provide an undesirable odor and can cause the stick to lose hardness and to become discolored.

Various stabilizing agents have been incorporated into gel antiperspirant sticks containing dibenzylidene alditols in an effort to minimize dibenzylidene alditol degradation. Examples include sodium hydroxide, potassium hydroxide, sodium carbonate, zinc acetate, zinc oxide, zinc carbonate, potassium carbonate, diethanolamine, triethanolamine, disodium succinate, sodium benzoate, sodium octanoate, hexamethylenetetramine, urea, 2-amino-2-methyl-1-propanol, magnesium sulfate, calcium hydroxide, and N-(2-hydroxyethyl) acetamide. These and other stabilizing agents, although apparently effective to some degree in stabilizing the dibenzylidene alditol, may have other problems associated with them. Sodium hydroxide and potassium hydroxide, for example, may provide a composition with an undesirable odor.

Because the dibenzylidene alditol is adversely affected by the presence of the antiperspirant salt, particularly at high temperatures, most prior art processes for making clear antiperspirant sticks generally keep these two components separated until the final process stage in order to minimize degradation of the dibenzylidene alditol. The most common method involves a two-phase procedure. That is, a first phase containing a portion of the vehicle and the gelling agent is heated to a temperature sufficient to dissolve the gelling agent (typically about 110°–115° C.), then cooled to about 100° C. A second phase containing a portion of the vehicle, the antiperspirant salt and the remaining ingredients is prepared and heated to about 60° to 70° C. The first phase and the second phase are then combined to form a mixture, which is poured into stick form molds and cooled to solidify. Examples of the two-phase process are illustrated in U.S. Pat. No. 4,154,816, U.S. Pat. No. 4,722,835, U.S. Pat. No. 4,781,917, U.S. Pat. No. 5,346,694, and U.S. Pat. No. 5,463,098 ( see Ex. 1). A variation of the two-phase process is disclosed in U.S. Pat. No. 5,376,363, where the dibenzylidene alditol powder is added to a hot solution of the liquid vehicle and antiperspirant salt. A further variation is disclosed in WO 95/18599, (U.S. Pat. No. 5,490,979), where multiple phases are continuously blended utilizing a multiple head metering pump or a twin screw extruder.

Generally speaking, virtually any method utilized to blend and heat the components when making clear gel sticks, including the aforementioned two-phase method, will be acceptable when performed with small quantities, such as on a laboratory scale. This is because a small scale process may be completed quickly, from start to finish, since small quantities may be heated and cooled relatively rapidly. When the dibenzylidene alditol is held at a high temperature for only a very brief period, particularly after the antiperspirant salt is added, its degradation is minimized. However, during commercial scale production, where batch sizes are greater than 200 kg and generally greater than 1000 kg, the overall process proceeds over a much longer period of time. Tanks of solutions may need to be maintained at high temperatures for relatively long periods before the last sticks from the batch are filled and cooled. Exposure of the dibenzylidene alditol to high temperatures, particularly in the presence of the antiperspirant salt, for more than a brief period causes its degradation. For this reason, commercially produced gel antiperspirant sticks containing a dibenzylidene alditol gelling agent do not have optimum clarity or odor characteristics.

SUMMARY OF THE INVENTION

The present invention features a method of making a gel cosmetic stick, particularly a clear gel cosmetic stick. The method Comprises first mixing a particulate dibenzylidene alditol with a liquid vehicle which contains an antiperspirant salt dissolved therein to form a uniform dispersion. The dibenzylidene alditol is mixed with the liquid vehicle at a temperature sufficiently low, preferably below 65° C., more preferably below 50° C., and most preferably below 35° C., so that substantially none of the dibenzylidene alditol dissolves in the liquid vehicle. This dispersion may comprise a commercial size quantity, typically greater than 200 kg, and optionally greater than 1000 kg. A portion of this dispersion, typically a relatively small portion, is then heated to a temperature sufficient to dissolve the dibenzylidene alditol therein, then cooled to form a gel. This heating and cooling is conducted sufficiently rapidly so as to minimize degradation of the dibenzylidene alditol. Preferably the heating and cooling is conducted such that said portion is subjected to a temperature greater than 90° C. for not more than two hours, more preferably not more than one hour, and most preferably not more than thirty minutes.

The present invention also embraces an intermediate composition for making a gel cosmetic stick. The intermediate comprises a dispersion of a particulate dibenzylidene alditol in a liquid vehicle which contains an antiperspirant salt dissolved therein, wherein substantially none of the dibenzylidene alditol is dissolved in the liquid vehicle. Preferably the dispersion comprises in percent by weight from 0.5 to 3%, more preferably 0.7 to 2%, of the dibenzylidene alditol, from 70 to 95%, more preferably 75 to 92%, of the liquid vehicle, and from 1 to 22%, more preferably 2 to 15%, of the antiperspirant salt. The liquid vehicle preferably comprises a polyhydric alcohol having from 3 to 6 carbon atoms and from 2 to 6 hydroxyl groups, and most preferably comprises propylene glycol.

The present invention further embraces a method of making a gel cosmetic stick which comprises heating a portion of the above-described intermediate to a temperature sufficient to dissolve the dibenzylidene alditol in that portion, and cooling that portion to form a gel. This heating and cooling is conducted sufficiently rapidly so as to minimize degradation of the dibenzylidene alditol. Preferably the heating and cooling is conducted such that said portion is subjected to a temperature greater than 90° C. for not more than two hours, more preferably not more than one hour, and most preferably not more than thirty minutes.

DETAILED DESCRIPTION OF THE INVENTION

A "clear" gel stick, as used herein, is a stick that is visually clear so that, like glass, it allows ready viewing of objects behind it. Preferred clear gel sticks have a turbidity measurement, expressed in Nephelometric Turbidity Units (NTU) of less than 150 NTU, more preferably less than about 100 NTU, and most preferably less than 80 NTU, when measured with a Hellige #965 Direct-Reading Turbidimeter. By "substantially free of off-odor" is meant that the gel stick (without any fragrance or fragrance masking agent) has an off-odor rating of 0 to 2, preferably 0 to 1, on a scale of 0 to 5 used by trained odor (or perfumery) experts, where 0 signifies no detectable off-odor and a rating of 4 to 5 is deemed unacceptable odor. By "stable" is meant that samples of the product, when stored at 45° C. for three months, will not exhibit any noticeable benzaldehyde odor or other off-odor (i.e. retains an odor rating of 0 to 2) and will not exhibit any significant change in clarity or color (i.e. retains a clarity of better than 150 NTU and a color of 0 to 2 on the yellowness scale). Yellowness is measured by spectrophotometer absorbence at 408 nm with 0 corresponding to 0 ppm ferric chloride in water and 5 corresponding to 500 ppm ferric chloride in water.

The method and intermediate of the present invention can be used to make gel sticks which comprise, as a minimum, a liquid vehicle, an antiperspirant salt dissolved in the vehicle, and a dibenzylidene alditol gelling agent. The liquid vehicle along with the gelling agent provide the matrix, or body, of the gel stick.

The preferred liquid vehicle comprises a polyhydric alcohol having from 3 to 6 carbon atoms and from 2 to 6 hydroxyl groups. Such polyhydric alcohols include diethylene glycol, triethylene glycol, dipropylene glycol, 1,2-propylene glycol, 1,3-propylene glycol, 2-methyl-1,3-propanediol, 1,4-butylene glycol, 1,2-butylene glycol, 1,3-butylene glycol, 2,3-butylene glycol, 2,4-dihydroxy-2-methylpentane, glycerin, sorbitol and the like, and mixtures thereof. Especially preferred are 1,2-propylene glycol (normally referred to simply as propylene glycol), dipropylene glycol, 2-methyl-1,3-propanediol, 1,3-butylene glycol, sorbitol and mixtures thereof. Most preferred as the liquid vehicle is propylene glycol, which may optionally include one or more of the aforementioned polyhydric alcohols. While the liquid vehicle may optionally include a monohydric alcohol such as ethanol, it is preferred that the liquid vehicle be substantially free of monohydric alcohol. While the liquid vehicle may also optionally contain a co-solvent for the gelling agent (e.g. N-methyl pyrrolidone), as described in the prior art, such is not preferred.

The gel stick generally includes between about 70% and about 95%, preferably between about 75% and about 92%, of the liquid vehicle by weight. A stick including an insufficient quantity of the liquid vehicle may be unclear or may provide an inadequate support matrix for the remainder of the components.

The dibenzylidene alditol is the gelling agent. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(meta-chlorobenzylidene) sorbitol. The preferred gelling agent is dibenzylidene sorbitol (DBS).

The gel stick generally contains between about 0.1% and about 5%, preferably between about 0.5% and about 3%, and most preferably between about 0.7% and about 2%, of the dibenzylidene alditol by weight. If the gel stick includes too much of the dibenzylidene alditol, it may lack sufficient clarity and/or may have an undesirable odor. If the gel stick includes too little of the dibenzylidene alditol it may lack sufficient hardness. A particularly advantageous feature of the present invention is the use of low levels (i.e. 1.5% or less) of the dibenzylidene alditol gelling agent, which results in sticks of exceptional clarity and odor-free characteristics.

The preferred gel stick will also optionally include a hydroxyalkyl cellulose as an additional gelling agent (or co-gellant), which provides the stick with adequate hardness even when the stick includes only a low level of the dibenzylidene alditol. The combined use of the co-gellant with reduced amounts of the dibenzylidene alditol (i.e. amounts of 1.5% or less) enable the production of gel sticks of exceptional clarity and stability. The preferred hydroxyalkyl cellulose co-gellants include alkyl groups with between one and five carbon atoms. The preferred co-gellant is hydroxypropylcellulose (e.g. Klucel HFF, Aqualon). Preferred gel sticks include between about 0.08% and about 1%, more preferably between about 0.1% and about 0.5%, most preferably between about 0.2% and about 0.4%, of the hydroxyalkyl cellulose by weight. If a hydroxyalkyl cellulose is included, it is preferably pre-dissolved in a portion of the liquid vehicle, then added to the other components.

Antiperspirant salts which may be used in the gel sticks of the present invention include any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the gel sticks of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

The antiperspirant salt is dissolved in the liquid vehicle or a portion of the liquid vehicle. Accordingly, it is preferred to utilize polyhydric alcohol solutions of antiperspirant salts. Especially preferred are solubilized salts which have been partially neutralized by addition of a pH-raising agent to a pH of about 4.1 to 5.0, preferably about 4.3 to 4.8. Particularly preferred neutralized antiperspirant salts are those which contain an additional alkaline glycinate, such as sodium, potassium, or zinc glycinate. Such solubilized antiperspirant salts are described in U.S. Pat. No. 5,643,558 entitled Method Of Making Polyhydric Alcohol Solutions Of Enhanced Efficacy Antiperspirant Actives (which corresponds to PCT/US95/14073), and in U.S. Pat. No. 5,463,098, the disclosures of which are incorporated herein by reference. An example of such a solubilized salt, which is partially neutralized with zinc glycinate, is Westchlor A2Z 8106 (Westwood Chemical Corp.). The preparation of a preferred solubilized antiperspirant salt is described in Example 1 below.

The additional alkaline glycinate which is preferably included in the solubilized antiperspirant salt raises the pH of the antiperspirant salt and, as a result, reduces the degradation of the dibenzylidene alditol in the gel stick. It is generally preferred to add sufficient alkaline glycinate to the solubilized antiperspirant salt so as to raise the pH of an approximately 10% aqueous solution of the antiperspirant salt to about 4.1 to 5.0, preferably about 4.3 to 4.8. (The 10% aqueous solution may be an approximately 50:50 polyhydric alcohol:water solution.) Preferred gel sticks which include such a partially neutralized salt will have a pH greater than 4.4, preferably about 4.7 to about 5.5, and more preferably about 4.8 to about 5.3. The pH of the finished stick can be measured by dissolving one part stick in ninety-nine parts water. The pH of the solubilized antiperspirant salt or of the resulting stick can, of course, be adjusted to the aforementioned preferred pH ranges with any pH-raising agent, or combination of pH-raising agents, provided that the agent or agents selected are soluble in the vehicle and do not adversely affect the clarity or odor characteristics of the stick to a significant extent.

Sufficient antiperspirant salt should be dissolved in the liquid vehicle so that the final composition, after all components are added, includes between about 1% and about 22%, preferably between about 2% and about 15%, of the antiperspirant salt by weight. It should be noted that reference throughout this application to weight percent of antiperspirant salt is intended to be calculated in accordance with the standard industry method, which includes bound water and glycine. This calculation compares with the new U.S. patent method, which excludes bound water and glycine, as follows:

| SALT | STANDARD METHOD | USP METHOD |
|---|---|---|
| Al—Zr—Gly in Prop. Glycol (Ex. 1) | 30% | 22% |
| Al—Zr—Gly in stick (Ex. 2) | 11% | 8.6% |

A gel stick made in accordance with the present invention will preferably include a chelating agent to improve its color and clarity. Examples of chelating agents include EDTA (ethylenediaminetetraacetate) salts such as Na$_4$EDTA and Na$_3$EDTA; hydroxyethylethylenediaminetriacetate (HEDTA); diethylenetriaminepentaacetate (DTPA); nitrilotriacetate (NTA); ethanoldiglycine disodium salt (EDG); diethanolglycine sodium salt (DEG); and 1,3-propylenediaminetetraacetic acid (PDTA). All of these are known and commercially available. Na$_4$EDTA and Na$_3$EDTA are preferred. The gel sticks generally include between about 0.05% and about 3%, preferably between about 0.1% and about 2%, of the chelating agent by weight. If too little chelating agent is included, the stick may have less clarity, an undesirable odor, and/or undesirable yellowness. If too much chelating agent is included, the clarity and/or other properties of the stick may be adversely affected. The chelating agent may reduce the color (in particular the yellow color) of the stick that can result, for example, from the presence of residual iron (or other metal contaminants) that may be present in the stick from a variety of sources. The gel stick preferably measures 0–1 on the yellowness scale.

The chelating agent may also act as a gelling agent stabilizer by increasing the pH of the stick, thus reducing or eliminating the need for other alkaline gelling agent stabilizers such as NaOH and KOH. The gel sticks preferably are substantially free of NaOH and KOH and, as a result, do not have the odor that can result from the interaction of these materials with the vehicle, particularly with propylene glycol. The elimination of other alkaline gelling agent stabilizers, particularly NaOH and KOH, is an advantageous feature of the present invention and is believed to substantially contribute to the odor-free characteristics of the gel sticks made in accordance with the present invention.

Suitable emollients may be incorporated into the gel stick to provide it with desirable application properties (smoothness, reduced tack, etc.). Examples of emollients include fatty acid esters such as isopropyl myristate and isopropyl palmitate; diesters of adipic, phthalic, and sebacic acids such as di-n-butyl phthalate, diisopropyl sebacate, diethyl sebacate, and diisopropyl adipate; propylene glycol diesters of short chain fatty acids; nonvolatile silicone oils such as dimethyl siloxane and dimethicone copolyol; volatile silicones such as Dow Corning 344 and Dow Corning 345 (available from Dow Corning), Silicone 7207 and Silicare 7158 (available from Union Carbide), and SF 1202 (available from General Electric); C$_{12}$–C$_{15}$ alcohol benzoates such as Finsolv (available from Finerex, Inc.); fatty alcohols such as cetyl alcohol and stearyl alcohol; alkyl ether derivatives of polyethylene glycols, polypropylene glycols and polypropylene polyethylene glycol copolymers such as PPG-5-Buteth-7, PPG-5-Ceteth-20, PPG-3-Isosteareth-9 and Glycereth-7-Diisononanoate. Many other examples of emollients are known in the art. The gel stick should include a sufficient quantity of emollient to provide the stick with the desired application properties without interfering with the clarity of the product. The preferred emollients should be soluble in the liquid vehicle and form a clear solution therein. The gel stick preferably includes less than about 10%, more preferably less than about 3%, and most preferably between about 0.25% and 1.25%, of emollients by weight.

The gel sticks can contain other optional conventional ingredients such as fragrances, humectants, hardeners such as waxes, fillers, colorants, preservatives, bactericides, UV absorbers, and the like. Obviously such materials should be selected so as not to adversely affect the clarity of the stick.

The method of the present invention comprises first mixing the particulate dibenzylidene alditol with the liquid vehicle which contains the antiperspirant salt dissolved therein to form a uniform dispersion. A variety of well-known techniques can be used to achieve a uniform dispersion and avoid clumps of the dibenzylidene alditol. For example, simply subjecting the dibenzylidene alditol/liquid vehicle mixture to sufficiently vigorous mixing conditions for a sufficient period of time may be all that is required to disperse the dibenzylidene alditol as relatively small, clump-free particles. The dispersal may, of course, be speeded up by shearing the mixture with an in-line shear device such as a high speed rotor-stator. While the dibenzylidene alditol may be added to the total quantity of liquid vehicle to be employed, it is preferable to first blend or disperse the dibenzylidene alditol with a portion of the liquid vehicle, then add that blend to a mixture of the remaining portion of vehicle and other optional components.

The dibenzylidene alditol is mixed with the liquid vehicle at a temperature sufficiently low, preferably below 65° C., more preferably below 50° C., most preferably below 35° C., and optimally below 30° C., so that substantially none of the dibenzylidene alditol dissolves in the liquid vehicle. It has been found that when maintained at relatively low temperatures, optimally below 30° C., this dispersion is surprisingly stable against degradation over relatively long periods, including up to several weeks. From a practical standpoint, this means that a commercial size quantity (i.e. a quantity greater than 200 kg, and typically greater than 1000 kg) can be maintained in a holding tank for a reasonable length of time (e.g. 4 to 24 hours or more) prior to being processed into gel sticks. This is contrary to the current practice in the art of minimizing the time as much as possible after the dibenzylidene alditol phase and the antiperspirant phase have been combined.

After preparation of the aforedescribed dispersion, a portion of it, typically a relatively small portion, is then heated to a temperature sufficient to dissolve the dibenzylidene alditol therein, then cooled to form a gel. This heating and cooling is conducted sufficiently rapidly so as to minimize degradation of the dibenzylidene alditol. Preferably the heating and cooling is conducted such that said portion is subjected to a temperature greater than 90° C. for not more than two hours, more preferably not more than one hour, most preferably not more than thirty minutes, and optimally not more than fifteen minutes. The higher the temperature utilized to effect complete dissolution of the dibenzylidene alditol, the shorter the overall residence time should be to minimize degradation.

Within these parameters it is possible to conduct the heating and cooling steps in a variety of ways. For example, a portion of the dispersion can be flash heated (e.g. in a heat exchanger) to a temperature at which the dibenzylidene alditol instantaneously dissolves (i.e. about 115° C.), then immediately cooled down (e.g. in another heat exchanger) to a pour (i.e. fill) temperature (typically about 2° to 18° C. above the set temperature, preferably about 90° C.), then poured (i.e. filled) into stick form molds and cooled to set.

Alternatively, the portion can be heated to and maintained at a temperature just warm enough to effect dissolution of the dibenzylidene alditol within a relatively short residence time (e.g. about 90° to 95° C. for about ten to twenty minutes), then poured (i.e. filled) into stick form molds and cooled to set. Either method can be performed on a continuous basis by pumping a stream of the dispersion continuously through one or more heat exchangers arranged to provide the temperatures and residence times as described above.

When the dibenzylidene alditol is mixed with the liquid vehicle and other optional components to form the uniform dispersion, this provides the intermediate for making a gel stick which is part of the present invention. The intermediate comprises a dispersion of a particulate dibenzylidene alditol in a liquid vehicle which contains an antiperspirant salt dissolved therein, wherein substantially none of the dibenzylidene alditol is dissolved in the liquid vehicle. Preferably the dispersion comprises in percent by weight from 0.5 to 3%, more preferably 0.7 to 2%, of the dibenzylidene alditol, from 70 to 95%, more preferably 75 to 92%, of the liquid vehicle, and from 1 to 22%, more preferably 2 to 15%, of the antiperspirant salt. The liquid vehicle preferably comprises a polyhydric alcohol having from 3 to 6 carbon atoms and from 2 to 6 hydroxyl groups, and most preferably comprises propylene glycol. The liquid vehicle may also include the various other optional components previously described which are desirable in the gel stick to be produced.

The following specific examples further illustrate the invention:

EXAMPLE 1

Antiperspirant Salt in Propylene Glycol

A 50% sodium glycinate solution was prepared by mixing 171 lbs. (77.6 kg) 50% NaOH with 67.8 lbs. (30.8 kg) water, then adding 160.3 lbs. (72.8 kg) of glycine (1:1 mole ratio of glycine to NaOH), the temperature rising from 25° to 30° C., then from 30° to 35° C., after the first and second additions respectively. To 103.3 lbs. (46.9 kg) of propylene glycol was added 7.8 lbs. (3.5 kg) of 50% sodium glycinate and the solution mixed for ten minutes. To this solution was added 33.9 lbs. (15.4 kg) of zirconium hydroxychloride glycinate (50% aqueous ZHC-gly solution with a Zr:gly ratio of about 1:1 ). After mixing this solution for about ten minutes, 255 lbs. (115.8 kg) of 10% ACH' solution (prepared by heating 10% ACH at about 80° C. for about 16 to 17 hours) was added and mixed for about ten minutes. This solution was preheated to about 70° to 75° C. and fed continuously to a type JHE flash evaporator (APV Crepaco Inc., Tonawanda, N.Y.; evaporator modified by mounting to the top of the flash chamber a 3 foot rectification tower filled with about 2.5 feet of 0.5 inch ceramic Berl saddles) maintained at about 60 mm Hg (absolute pressure) from which was withdrawn at about 1 gal/hr a clear solution comprising 65% propylene glycol, 30% enhanced efficacy aluminum-zirconium tetrachlorohydrate-glycine (more than 80% of aluminum in peaks 3 and 4 with peak 4 to peak 3 area ratio greater than 1 and Gly:Zr ratio about 1.6:1), and 5% water. The pH of a sample of this solution diluted with an equal portion of distilled water was about 4.7. This antiperspirant salt solution is incorporated into the following examples in which gel sticks are made using the method of the present invention.

EXAMPLES 2 AND 3

| Ingredient | Ex. 2 Wt. % | Ex. 3 Wt. % |
|---|---|---|
| Propylene glycol | 85.50 | 84.70 |
| Al/Zr tetrachlorohydrate-gly | 11.00* | 11.00* |
| Dibenzylidene sorbitol | 1.00 | 1.30 |
| Hydroxypropyl cellulose | 0.30 | 0.30 |
| Fragrance | 1.25 | 1.25 |
| Diisopropyl sebacate | — | 1.00 |
| Glycereth-7-diisononanoate | 0.50 | — |
| Dimethicone copolyol (ABIL B 8851) | 0.25 | 0.25 |
| Na$_4$EDTA | 0.20 | 0.20 |

*Weight % of salt in final composition. Salt is added in solubilized form as prepared in Example 1.

Examples 2 and 3 are prepared according to the following procedure.

A first pre-mix is made by dissolving the hydroxypropyl cellulose in about 73% of the total propylene glycol mass (excluding that which is part of the antiperspirant salt solution) at a temperature of about 95° C. in a first pre-mix tank. This is mixed for about two to three hours to ensure complete dissolution, then cooled to below 30° C. A second pre-mix is made by dispersing the dibenzylidene sorbitol in about 9% of the total propylene glycol mass (excluding that which is part of the antiperspirant salt solution) at a temperature below 30° C. in a second pre-mix tank using an IKA Dispax Reactor as a shear device.

The remaining propylene glycol is added to a main mix tank at ambient temperature (below 30° C.), then the Na$_4$EDTA is added and mixed in thoroughly. To this solution is added with mixing at ambient temperature (below 30° C.) the antiperspirant salt solution in propylene glycol (as prepared in Example 1 ), the emollients, the first pre-mix (hydroxypropyl cellulose dissolved in propylene glycol), the second pre-mix (DBS dispersed in propylene glycol), and the fragrance.

The above dispersion or slurry is continuously drawn from the mix tank and pumped through a shell-and-tube heat exchanger which heats the stream of dispersion to about 90° C. The heated material exits the heat exchanger into a small heated tank where a holdup volume is maintained at about 90° C. for about a ten minute residence time to insure complete dissolution of the dibenzylidene sorbitol in the vehicle. This solution is then continuously pumped to a filler which fills stick form molds that are subsequently cooled in a cooling tunnel maintained at about 13° C. to form solid gel sticks. The heating, holding, filling and cooling equipment are arranged so that no portion of the dispersion is subjected to a temperature greater than 90° C. for more than fifteen minutes.

EXAMPLES 4 AND 5

| Ingredient | Ex. 4 Wt. % | Ex. 5 Wt. % |
|---|---|---|
| Propylene glycol | 86.00 | 85.65 |
| Hydroxypropyl cellulose | 0.30 | 0.20 |
| Dibenzylidene sorbitol | 0.50 | 0.95 |
| Al/Zr tetrachlorohydrate-gly | 11.00* | 11.00* |
| Na$_4$EDTA | 0.20 | 0.20 |
| Glycereth-7-diisononanoate | 0.50 | 0.50 |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

Examples 4 and 5 are prepared by procedures analogous to the procedure used to prepare examples 2 and 3.

EXAMPLES 6 AND 7

| Ingredient | Ex. 6 Wt. % | Ex. 7 Wt. % |
|---|---|---|
| Propylene glycol | 85.00 | 84.80 |
| Al/Zr tetrachlorohydrate-gly | 11.00* | 11.00* |
| Dibenzylidene sorbitol | 1.20 | 1.50 |
| Hydroxypropyl cellulose | 0.30 | — |
| Fragrance | 1.25 | 1.25 |
| Diisopropyl sebacate | 1.00 | 1.00 |
| Dimethicone copolyol (ABIL B 8851) | 0.25 | 0.25 |
| Na$_4$EDTA | — | 0.20 |

*Weight % of salt in final composition. Salt is added in solubilized form as prepared in Example 1.

Examples 6 and 7 are prepared by procedures analogous to the procedure used to prepare examples 2 and 3, except that in the case of example 7 a first pre-mix is not necessary.

EXAMPLE 8

| Ingredient | Wt. % |
|---|---|
| Propylene glycol | 84.85 |
| Hydroxypropyl cellulose | 0.35 |
| Dibenzylidene sorbitol | 1.10 |
| Al/Zr tetrachlorohydrate-gly | 11.00* |
| Diisopropyl sebacate | 1.00 |
| Dimethicone copolyol (ABIL B 8851) | 0.25 |
| Na$_4$EDTA | 0.20 |
| Fragrance | 1.25 |

*Weight % of salt in final composition. Salt is added in solubilized form as prepared in Example 1.

Example 8 is prepared by a procedure analogous to the procedure used to prepare examples 2 and 3.

EXAMPLE 9

| Ingredient | Wt. % |
|---|---|
| Propylene glycol | 92.75 |
| Al/Zr tetrachlorohydrate-gly | 3.00* |
| Na$_4$EDTA | 0.20 |
| Dibenzylidene sorbitol | 1.30 |
| Hydroxypropyl cellulose | 0.50 |
| Oleth-10 | 0.75 |
| PPG-10 butanediol | 0.75 |
| PPG-3 myristyl ether | 0.75 |

*Weight % of salt in final composition. Salt is added in solubilized form as prepared in Example 1.

Example 9 is prepared by a procedure analogous to the procedure used to prepare examples 2 and 3.

EXAMPLE 10

| Ingredient | Wt. % |
|---|---|
| Propylene glycol | 91.35 |
| Al/Zr tetrachlorohydrate-gly | 6.00* |
| Dibenzylidene sorbitol | 1.90 |
| Glycereth-7-diisononanoate | 0.50 |
| Dimethicone copolyol (ABIL B 8851) | 0.25 |

*Weight % of salt in final composition. Salt is added in solubilized form as prepared in Example 1.

All of the components except the DBS are added to a mixing tank and stirred at ambient temperature (below 30°

C.). The DBS is then added and the mixture stirred for several hours to form a uniform dispersion. This dispersion is drawn from the tank on a continuous basis where the stream is flash heated to about 115°–118° C. in a first heat exchanger to instantaneously dissolve the DBS, then immediately cooled to about 90° C. in a second heat exchanger, after which the solution is continuously filled into stick form molds and cooled to solidify. The flash heating, cooling and filling equipment are arranged so that no portion of the dispersion is subjected to a temperature greater than 90° C. for more than ten minutes.

What is claimed is:

1. A method of making a gel cosmetic stick which comprises mixing, at a temperature below 50° C., a particulate dibenzylidene alditol with a liquid vehicle which contains an antiperspirant salt dissolved therein to form a uniform dispersion, heating a portion of said dispersion to a temperature sufficient to dissolve the dibenzylidene alditol in said portion, and cooling said portion to form a gel.

2. The method of claim 1 wherein said mixing is conducted at a temperature below 35° C.

3. The method of claim 1 wherein said mixing is conducted at a temperature sufficiently low so that substantially none of the dibenzylidene alditol dissolves in the liquid vehicle.

4. The method of claim 1, 2 or 3 wherein said heating and cooling is conducted sufficiently rapidly so as to minimize degradation of the dibenzylidene alditol.

5. The method of claim 4 wherein said heating and cooling is conducted such that said portion is not subjected to a temperature greater than 90° C. for more than two hours.

6. The method of claim 4 wherein said heating and cooling is conducted such that said portion is not subjected to a temperature greater than 90° C. for more than one hour.

7. The method of claim 4 wherein said heating and cooling is conducted such that said portion is not subjected to a temperature greater than 90° C. for more than thirty minutes.

8. The method of claim 6 wherein said cooling comprises first cooling said portion to a temperature of about 2° C. to about 18° C. above its set point, pouring said portion into stick form molds, then further cooling to form a gel.

9. The method of claim 4 wherein said uniform dispersion comprises a quantity greater than 200 kg and comprises in percent by weight from 0.5 to 3% of said dibenzylidene alditol, from 70 to 95% of said liquid vehicle, and from 1 to 22% of said antiperspirant salt, and said liquid vehicle comprises a polyhydric alcohol having from 3 to 6 carbon atoms and from 2 to 6 hydroxyl groups.

10. The method of claim 9 wherein said dibenzylidene alditol comprises dibenzylidene sorbitol, said liquid vehicle comprises propylene glycol, and said antiperspirant salt comprises aluminum-zirconium chlorohydrate.

11. The method of claim 10 wherein said uniform dispersion additionally comprises 0.1 to 1% of a hydroxyalkyl cellulose.

12. A method of making a gel cosmetic stick which comprises mixing at a temperature below 50° C. a particulate dibenzylidene alditol with a liquid vehicle to form a uniform dispersion, wherein said liquid vehicle comprises a polyhydric alcohol having from 3 to 6 carbon atoms and from 2 to 6 hydroxyl groups with an antiperspirant salt dissolved therein, wherein said uniform dispersion comprises in percent by weight from 0.5 to 3% of said dibenzylidene alditol, from 70 to 95% of said liquid vehicle, and from 1 to 22% of said antiperspirant salt, heating a portion of said dispersion to a temperature sufficient to dissolve the dibenzylidene alditol in said portion, and cooling said portion to form a gel, wherein said heating and cooling is conducted such that said portion is not subjected to a temperature greater than 90° C. for more than thirty minutes.

13. The method of claim 12 wherein said mixing is conducted at a temperature below 35° C., said uniform dispersion comprises a quantity greater than 200 kg, and said heating and cooling is conducted continuously on a stream of said dispersion such that no portion is subjected to a temperature greater than 90° C. for more than fifteen minutes.

14. The method of claim 13 wherein said uniform dispersion comprises in percent by weight from 0.7 to 2% of said dibenzylidene alditol, from 75 to 92% of said liquid vehicle, and from 2 to 15% of said antiperspirant salt.

15. The method of claim 12 or 14 wherein said dibenzylidene alditol comprises dibenzylidene sorbitol, said liquid vehicle comprises propylene glycol, and said antiperspirant salt comprises aluminum-zirconium chlorohydrate.

16. The method of claim 15 wherein said uniform dispersion additionally comprises 0.1 to 1% of a hydroxyalkyl cellulose.

17. An intermediate for making a gel cosmetic stick which intermediate comprises a dispersion of a particulate dibenzylidene alditol in a liquid vehicle which contains an antiperspirant salt dissolved therein, wherein substantially none of the dibenzylidene alditol is dissolved in said liquid vehicle.

18. The intermediate of claim 17 wherein said dispersion comprises in percent by weight from 0.5 to 3% of said dibenzylidene alditol, from 70 to 95% of said liquid vehicle, and from 1 to 22% of said antiperspirant salt, and said liquid vehicle comprises a polyhydric alcohol having from 3 to 6 carbon atoms and from 2 to 6 hydroxyl groups.

19. The intermediate of claim 18 wherein said dispersion comprises in percent by weight from 0.7 to 2% of said dibenzylidene alditol, from 75 to 92% of said liquid vehicle, and from 2 to 15% of said antiperspirant salt.

20. The intermediate of claim 18 or 19 wherein said dibenzylidene alditol comprises dibenzylidene sorbitol, said liquid vehicle comprises propylene glycol, and said antiperspirant salt comprises aluminum-zirconium chlorohydrate.

21. The intermediate of claim 22 wherein said dispersion comprises a quantity greater than 200 kg.

22. The intermediate of claim 18 or 19 wherein said dispersion comprises a quantity greater than 200 kg.

23. A method of making a gel cosmetic stick which comprises heating a portion of the intermediate of claim 18 to a temperature sufficient to dissolve the dibenzylidene alditol in said portion, and cooling said portion to form a gel, wherein said heating and cooling is conducted such that said portion is not subjected to a temperature greater than 90° C. for more than thirty minutes.

* * * * *